(12) United States Patent
　　　Okuda

(10) Patent No.: US 10,893,958 B2
(45) Date of Patent: **\*Jan. 19, 2021**

(54) MULTI-ARTICULATED LINK KNEE JOINT

(71) Applicant: NABTESCO CORPORATION, Tokyo (JP)

(72) Inventor: Masahiko Okuda, Kobe (JP)

(73) Assignee: NABTESCO CORPORATION, Tokyo (JP)

( * ) Notice: Subject to any disclaimer, the term of this patent is extended or adjusted under 35 U.S.C. 154(b) by 67 days.

This patent is subject to a terminal disclaimer.

(21) Appl. No.: 16/249,248

(22) Filed: Jan. 16, 2019

(65) Prior Publication Data

US 2019/0262144 A1　　Aug. 29, 2019

(30) Foreign Application Priority Data

Feb. 28, 2018　(JP) .................................. 2018-035537

(51) Int. Cl.
　　*A61F 2/64*　　(2006.01)
　　*A61F 2/70*　　(2006.01)
　　*A61F 2/50*　　(2006.01)

(52) U.S. Cl.
　　CPC ................ *A61F 2/644* (2013.01); *A61F 2/70* (2013.01); *A61F 2002/5038* (2013.01)

(58) Field of Classification Search
　　CPC .... A61F 2/24; A61F 2/64; A61F 2/642; A61F 2/643; A61F 2/644; A61F 2/645; A61F 2/646; A61F 2002/6863; A61F 2002/6818
　　See application file for complete search history.

(56) References Cited

U.S. PATENT DOCUMENTS

2015/0032228 A1\* 1/2015 Shirata ...................... A61F 2/76
　　　　　　　　　　　　　　　　　　　　　　　　　　　　　　623/39
2019/0314172 A1\* 10/2019 Okuda ................... G01D 5/142

FOREIGN PATENT DOCUMENTS

WO　　　2013132662 A1　　9/2013

\* cited by examiner

*Primary Examiner* — Bruce E Snow
(74) *Attorney, Agent, or Firm* — Cantor Colburn LLP

(57) ABSTRACT

A multi-articulated link knee joint includes: a knee unit in which an upper link member is structured to rotate relative to a lower link member by a multi-articulated link mechanism including a plurality of link members including the upper link member and the lower link member; a driven member to move in accordance with the rotation of the upper link member; a position detector for detecting the position of the driven member, the position detector provided at the lower link member; and an angle detector for obtaining the bending angle of the knee unit from the position of the driven member.

5 Claims, 21 Drawing Sheets

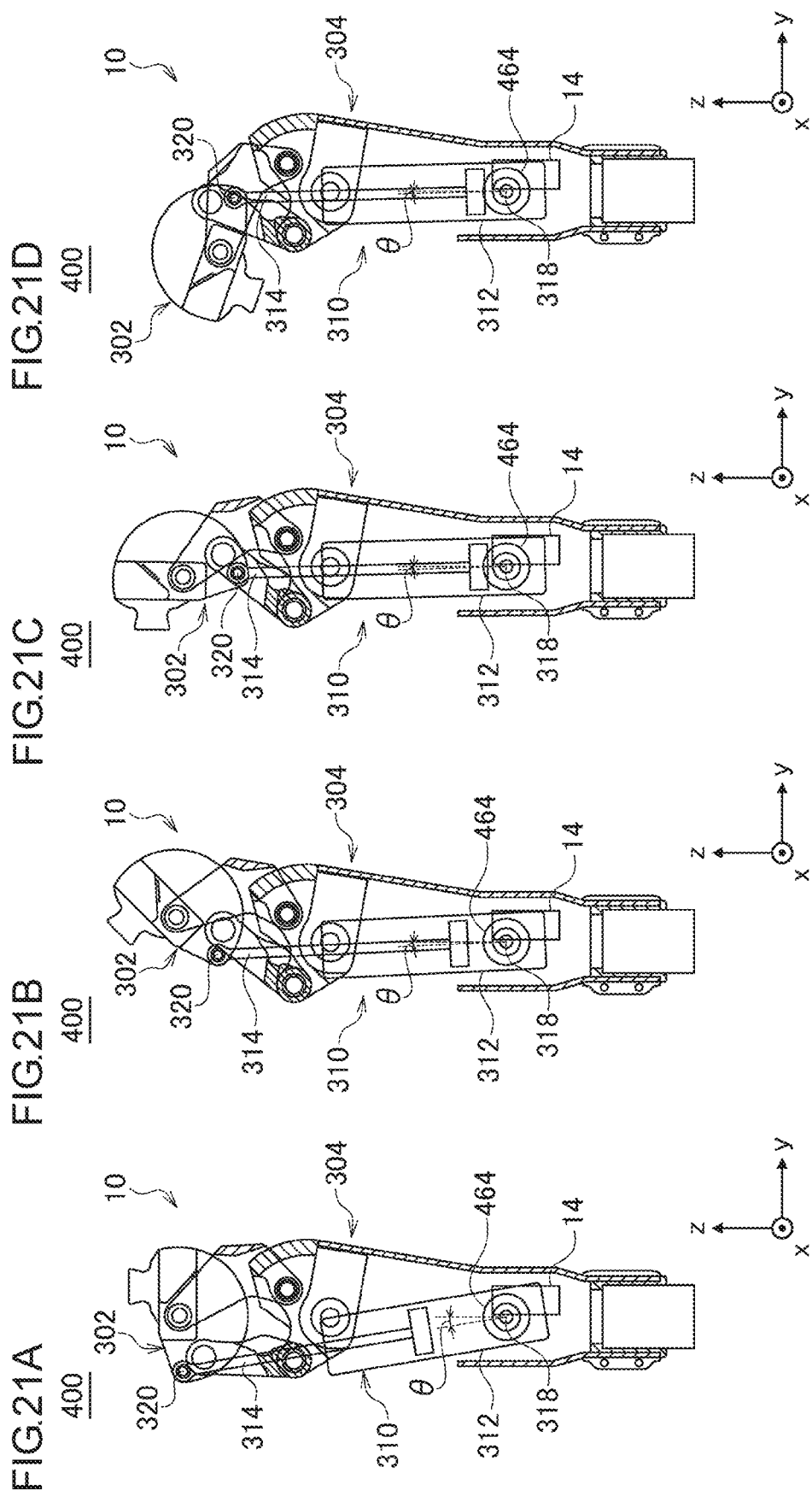

MULTI-ARTICULATED LINK KNEE JOINT

BACKGROUND OF THE INVENTION

1. Field of the Invention

The present invention relates to a multi-articulated link knee joint.

2. Description of the Related Art

Prosthetic legs used by people who had have their thigh cut above their knee due to a disease or an accident are coupled with an artificial knee joint that bends like a knee joint of a living body. When the artificial knee joint is bent depending on the motion of the user, motions such as standing, sifting, and walking are made possible.

Patent document 1 discloses an artificial knee joint including a knee unit that bends by a multi-articulated link mechanism and an air cylinder that assists the motion of the knee unit depending on the bending angle. In this artificial knee joint, since the multi-articulated link mechanism allows the motion of the knee unit to be similar to that of the knee joint of a living body, more natural motion is made possible. In addition, since the walking motion is supported by the air cylinder, the stability of walking is improved.

[Patent document 1] WO2013/132662

The knee joint according to International Publication No. 2013/132662 detects the position of a piston rod connected to the knee unit, and a bending angle of the knee unit is obtained from the detection result to control an air cylinder. Other than air cylinders or hydraulic cylinders, there are cases where rotary hydraulic dampers having no piston rod are used as auxiliary drivers for assisting the motion of the knee unit. In this case, there is a need to change the configuration related to detection of the bending angle. If the configuration related to detection of the bending angle can be adapted to be compatible with auxiliary drivers of different types, there is a possibility that cost can be reduced by sharing parts in deploying various product groups.

SUMMARY OF THE INVENTION

The present invention has been made in view of these challenges, and it is an object of the present invention to adapt a configuration for detecting a bending angle of a knee unit in a multi-articulated link knee joint to be compatible with auxiliary drivers of a plurality of types.

One embodiment of the present invention is a multi-articulated link knee joint. This multi-articulated link knee joint includes: a knee unit in which an upper link member rotates relative to a lower link member by a multi-articulated link mechanism including a plurality of link members including the upper link member and the lower link member; a driven member moving in accordance with rotation of the upper link member; a position detector for detecting the position of the driven member, the position detector provided at one of the plurality of link members; and an angle detector for obtaining the bending angle of the knee unit from the position of the driven member.

According to this embodiment, the position of the driven member moving in accordance with the rotation of the upper link member is detected, and the bending angle of the knee unit is obtained from the detection result, and thus auxiliary drivers of different types can be covered by similar configurations.

BRIEF DESCRIPTION OF THE DRAWINGS

FIG. 21A to FIG. 21D are diagrams illustrating how a knee unit is bent.

DETAILED DESCRIPTION OF THE INVENTION

Figure 1:
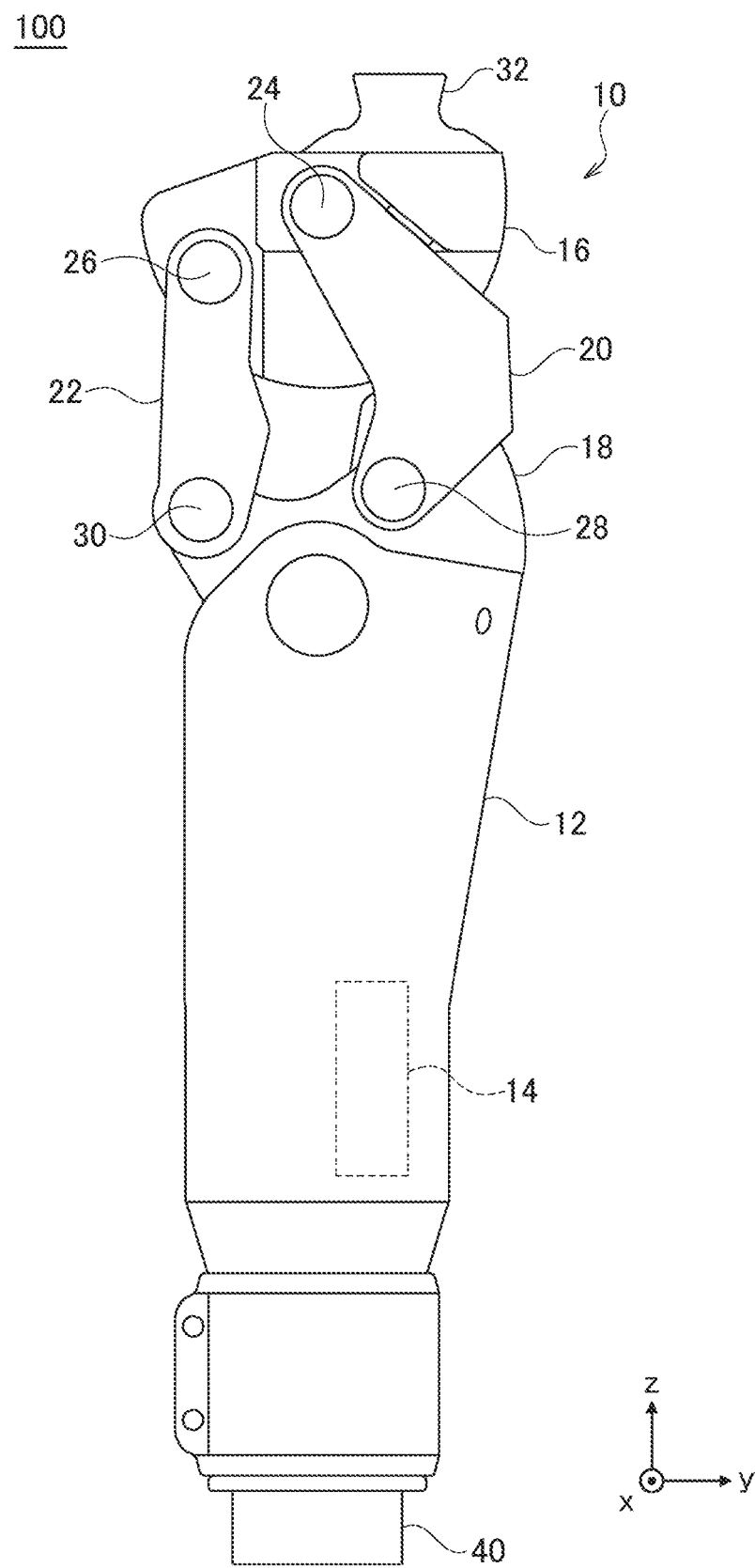
FIG. 1 is a side view of a multi-articulated link knee joint according to an embodiment.

Hereinafter, in embodiments, the same component is denoted by the same symbol, and redundant explanations are omitted. In addition, for convenience of explanation, a part of a component is omitted as appropriate in the drawings.

Before specifically explaining a multi-articulated link knee joint according to an embodiment, the overview will be explained. A multi-articulated link knee joint according to an embodiment includes a knee unit in which an upper link rotates with respect to a lower link by a multi-articulated link mechanism and an auxiliary driver for assisting the motion of the knee unit. An example of the auxiliary driver is a rotary hydraulic damper. The knee unit includes a driven member that moves in accordance with the rotation of the upper link and a position detector that detects the position of the driven member. The bending angle of the knee unit can be obtained from a detection result of the position detector from the relationship between a preset position of the driven member and the bending angle of the knee unit. The auxiliary driver may be a cylinder device such as an air cylinder or a hydraulic cylinder. Auxiliary drivers of different types can be covered by similar configurations to detect the bending angle of a knee unit.

Figure 2:
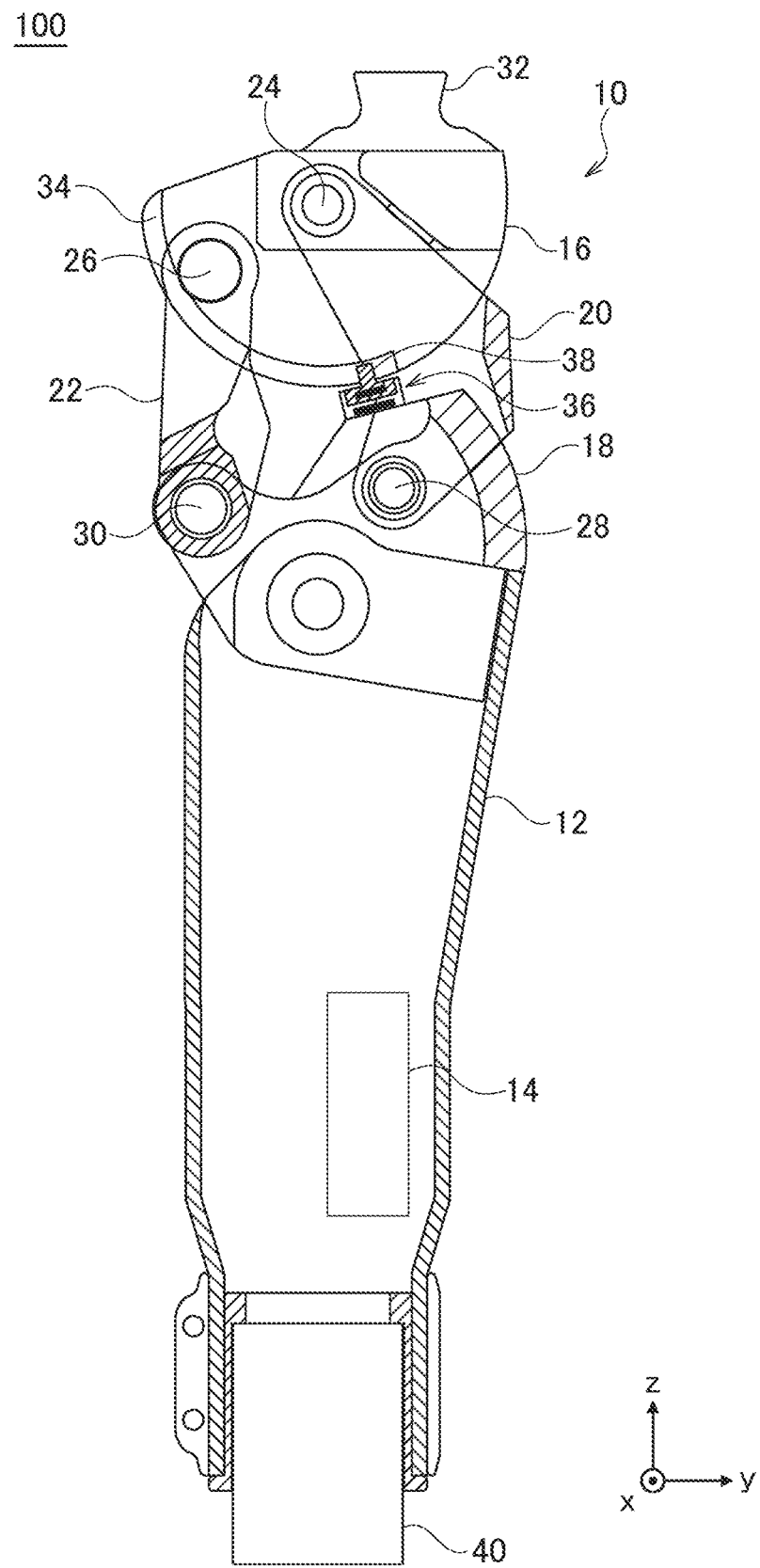
FIG. 2 is a schematic cross-sectional view of the multi-articulated link knee joint according to the embodiment.

FIG. 1 is a side view of a multi-articulated link knee joint 100 according to an embodiment. FIG. 2 is a schematic cross-sectional view of the multi-articulated link knee joint 100. In the following description, in an xyz orthogonal coordinate system illustrated in each drawing, a direction parallel to the x axis is defined as the lateral direction, and the positive direction of the x axis is referred to as "left" with the negative direction referred to as "right." A direction parallel to the y axis is defined as the anterior-posterior direction, and the positive direction of the y axis is referred to as "anterior" with the negative direction referred to as "posterior." A direction parallel to the z axis is defined as the vertical direction, and the positive direction of the z axis is referred to as "up" with the negative direction referred to as "down."

The multi-articulated link knee joint 100 includes a knee unit 10, a lower leg part 12, and a control device 14. The knee unit 10 is bent by a multi-articulated link mechanism including an upper link 16, a lower link 18, an anterior link 20, and a posterior link 22. A first shaft 24 and a second shaft 26 are provided at the upper link 16, and a third shaft 28 and a fourth shaft 30 are provided at the lower link 18. Each of the shafts is provided such that the axial direction thereof is parallel to the x axis and so as to be rotatable. The anterior link 20 is attached to the ends of the first shaft 24 and the third shaft 28. The posterior link 22 is attached to the ends of the second shaft 26 and the fourth shaft 30. The upper link 16 is supported by the anterior link 20 and the posterior link 22 and rotates with respect to the lower link 18. The thigh connector 32 protruding from the upper link 16 is connected to a socket attached to the thigh of a user. An angle formed by the direction in which the thigh connector 32 protrudes and the z axis is defined as the bending angle of the knee unit 10. The bending angle illustrated in FIG. 1 and FIG. 2 is 0°, which is a state in which the knee unit 10 is completely extended.

Figure 3:
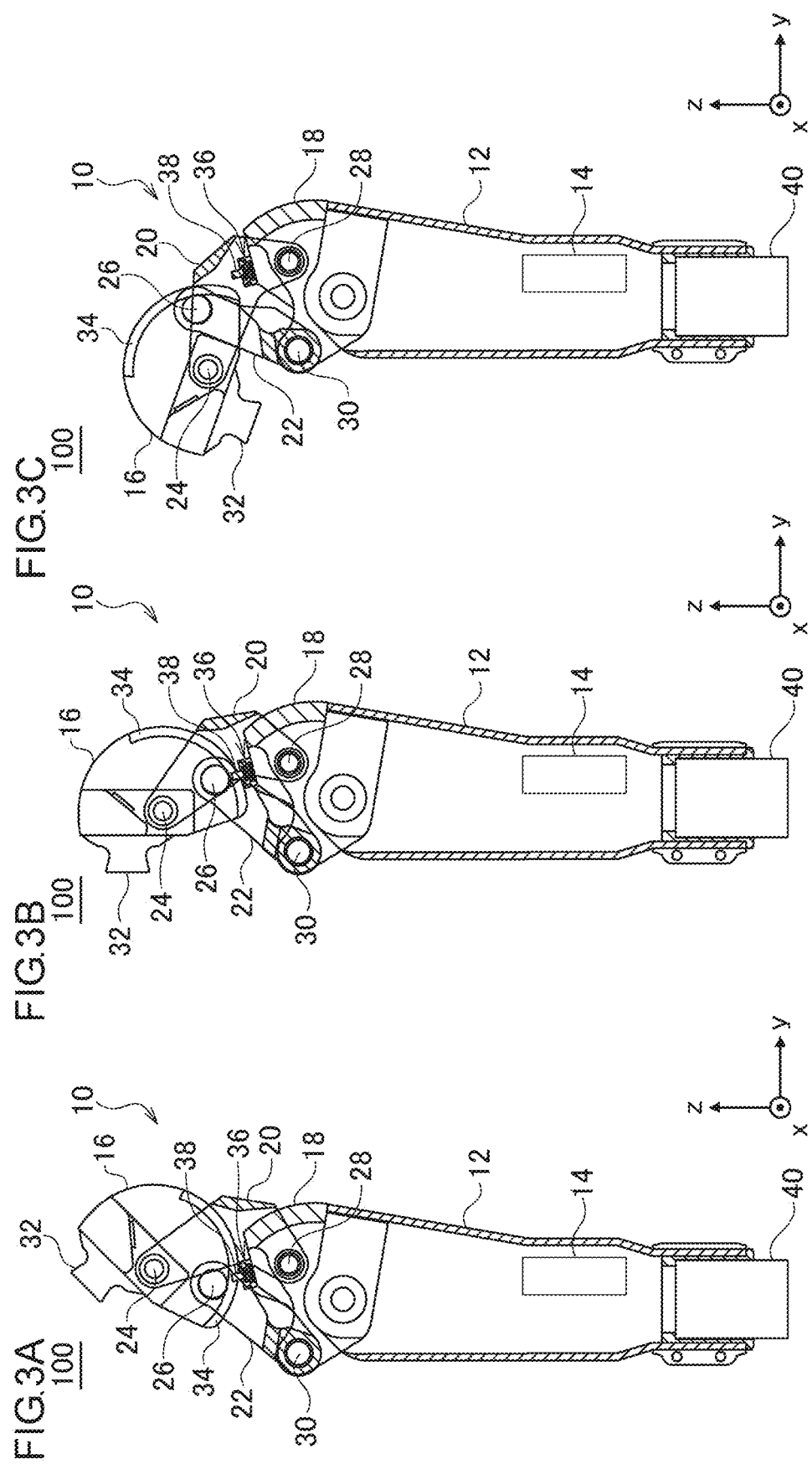
FIG. 3A to FIG. 3C are views illustrating how a knee unit of the multi-articulated link knee joint according to the embodiment is bent.

FIG. 3A to FIG. 3C are views illustrating how the knee unit 10 is bent. The bending angles of the knee unit 10 illustrated in FIG. 3A to FIG. 3C are 45°, 90°, and 160°, respectively. When the bending angle is large, the anterior link 20 and the posterior link 22 intersect. The upper link 16 rotates while moving backward with respect to the lower link 18. Due to the rotation of the upper link 16, the knee unit 10 bends like the knee joint of a living body does.

A groove 34 extending in the rotation direction of the upper link 16 is formed on the outer circumferential surface of the upper link 16 on the lower link 18 side. The groove 34 is a moving mechanism to move a driven member which will be described later in accordance with the rotation of the upper link 16. A rotation detector 36 for detecting the rotation of the upper link 16 is provided on the lower link 18. The rotation detector 36 includes a driven member 38. The driven member 38 fits into the groove 34 and moves in the x axis direction in accordance with the rotation of the upper link 16. The rotation detector 36 outputs a detection value corresponding to the position of the driven member 38 to the control device 14. The structure of the groove 34 and the rotation detector 36 will be described later.

The lower leg part 12 is formed in a cylindrical shape and accommodates the control device 14. The lower link 18 is secured onto the lower leg part 12. Furthermore, provided under the lower leg part 12 is a leg connector 40 which is connected to a leg part included in a prosthetic leg. The control device 14 obtains the bending angle of the knee unit 10 from a detection result of the rotation detector 36 and controls an auxiliary driver (not illustrated).

Note that, in this specification, a link and members secured to the link to move in conjunction with the link are collectively referred to as a "link member." For example, "upper link member" includes the upper link 16 and the thigh connector 32. A "lower link member" includes the lower link 18 and the lower leg part 12. The multi-articulated link mechanism of the multi-articulated link knee joint 100 includes a plurality of link members including the upper link member and the lower link member.

Figure 4:
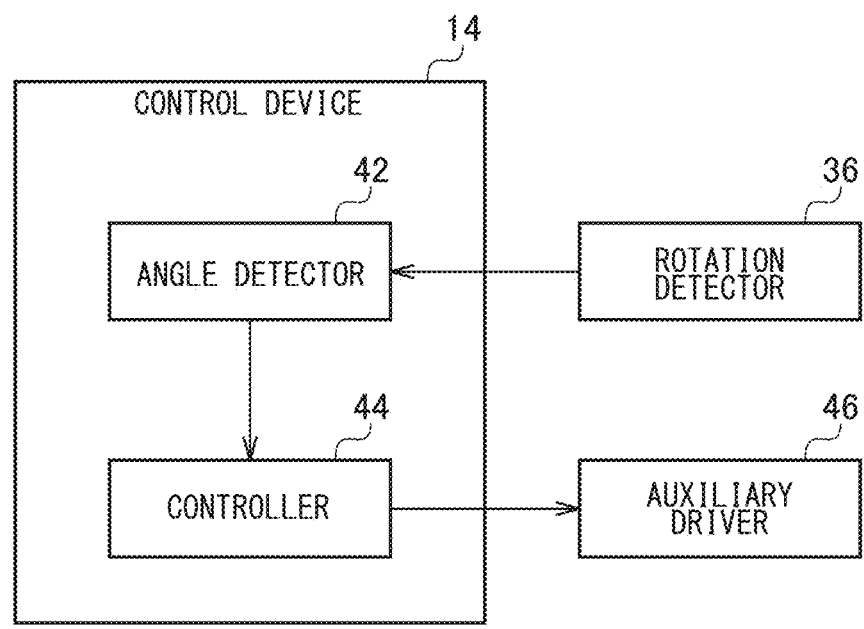
FIG. 4 is a block diagram illustrating a functional configuration of a control device according to the embodiment.

FIG. 4 is a block diagram illustrating a functional configuration of the control device 14 according to the embodiment. Each of the blocks illustrated herein in the block diagram can be implemented by an element or a mechanical device including a CPU of a computer from the perspectives of hardware and, from the perspectives of software, by a computer program or the like. In this example, functional blocks implemented by coordination thereof are illustrated. Therefore, it should be understood by a person skilled in the art that these functional blocks can be implemented by various forms by hardware, software, or a combination thereof.

The control device 14 includes an angle detector 42 and a controller 44. The angle detector 42 obtains the bending angle of the knee unit 10 from a detection result of the rotation detector 36. The controller 44 controls an auxiliary driver 46 in accordance with the bending angle obtained by the angle detector 42. In the present embodiment, the auxiliary driver 46 is a rotary hydraulic damper attached to the first shaft 24 and is controlled by the controller 44 to assist the motion of the knee unit 10. The controller 44 controls the auxiliary driver 46 so as to limit the rotation of the third shaft 28 when the bending angle is close to 0°. This prevents knee bending, that is, the knee unit 10 bent against the will of the user. In addition, when the leg is in a swinging state in which the bending angle changes such as when walking, the auxiliary driver 46 is controlled so as to rotate the third shaft 28 in accordance with the angle-changing direction. As a result, the lower leg part 12 swings in accordance with kicking-out of the leg, and thus the user can walk comfortably. Note that the rotary hydraulic damper serving as the auxiliary driver 46 may be provided at any one of the second shaft 26, the third shaft 28, and the fourth shaft 30. However, since there are times that the rotation direction of the third shaft 28 and the fourth shaft 30 is reversed during rotation of the upper link 16, the rotary hydraulic damper is more easily controlled when provided at the first shaft 24 or the second shaft 26 that rotates always in the same direction as the upper link 16 does. Alternatively, a cylinder device such as an air cylinder or a hydraulic cylinder may be provided as the auxiliary driver 46.

Figure 5A:
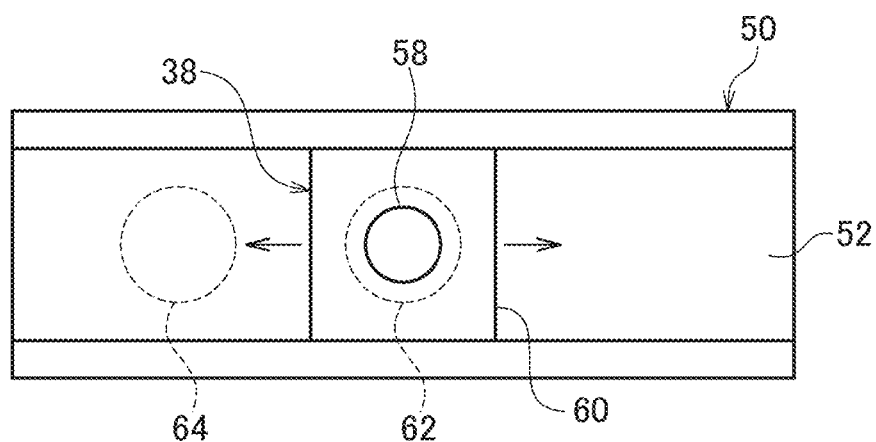
FIG. 5A and FIG. 5B are views illustrating a configuration of a rotation detector according to an embodiment.
Figure 5B:
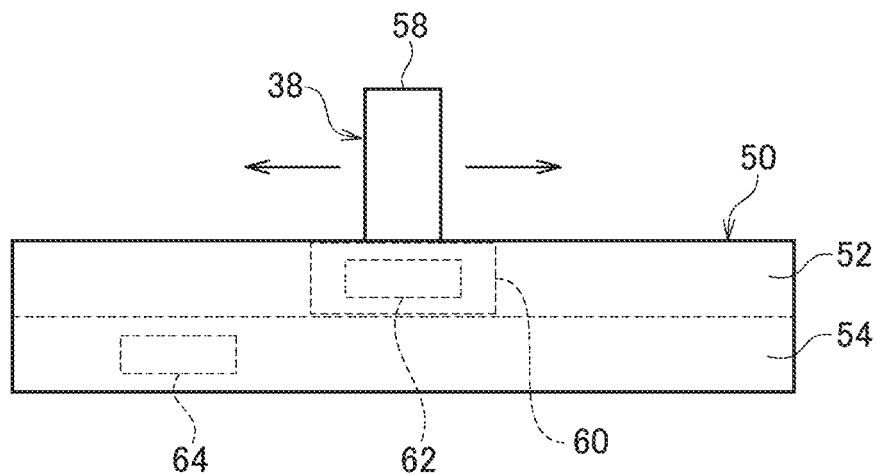

FIG. 5A and FIG. 5B are views illustrating the structure of the rotation detector 36 according to the embodiment. FIG. 5A is a top view of the rotation detector 36, and FIG. 5B is a side view of the rotation detector 36. The rotation detector 36 includes the driven member 38, a case 50, and a position detector 64. The driven member 38 includes a protrusion 58 and a main body 60 that are integrally formed. The protrusion 58 is formed in a cylindrical shape and protrudes from the main body 60. The main body 60 is formed into a rectangular parallelepiped shape and accommodates a magnet 62. The case 50 includes an upper case 52 and a lower case 54. The upper case 52 forms a rail that allows the driven member 38 to move in the directions indicated by the arrows. The lower case 54 accommodates the position detector 64. The position detector 64 includes a Hall element and outputs a detection value corresponding to the distance to the magnet 62.

The protrusion 58 of the driven member 38 fits into the groove 34 of the upper link 16. When the upper link 16 rotates, the protrusion 58 is pushed by the groove 34, and the driven member 38 moves in one of the directions indicated by the arrows. Due to the movement of the driven member 38, the distance between the magnet 62 and the position detector 64 changes. The position detector 64 outputs a detection value corresponding to the position of the driven member 38, that is, the bending angle of the knee unit 10. The rotation detector 36 is attached to the lower link 18 such that the moving direction of the driven member 38 and the axial directions of the respective axes of the knee unit 10 are parallel to each other. Note that the moving direction of the driven member 38 may be inclined with respect to the direction of rotation axis of the knee unit 10. By allowing the moving direction of the driven member 38 parallel to the direction of rotation axes as in the present embodiment, the moving amount of the driven member 38 can be reduced to downsize the rotation detector 36.

Figure 6:
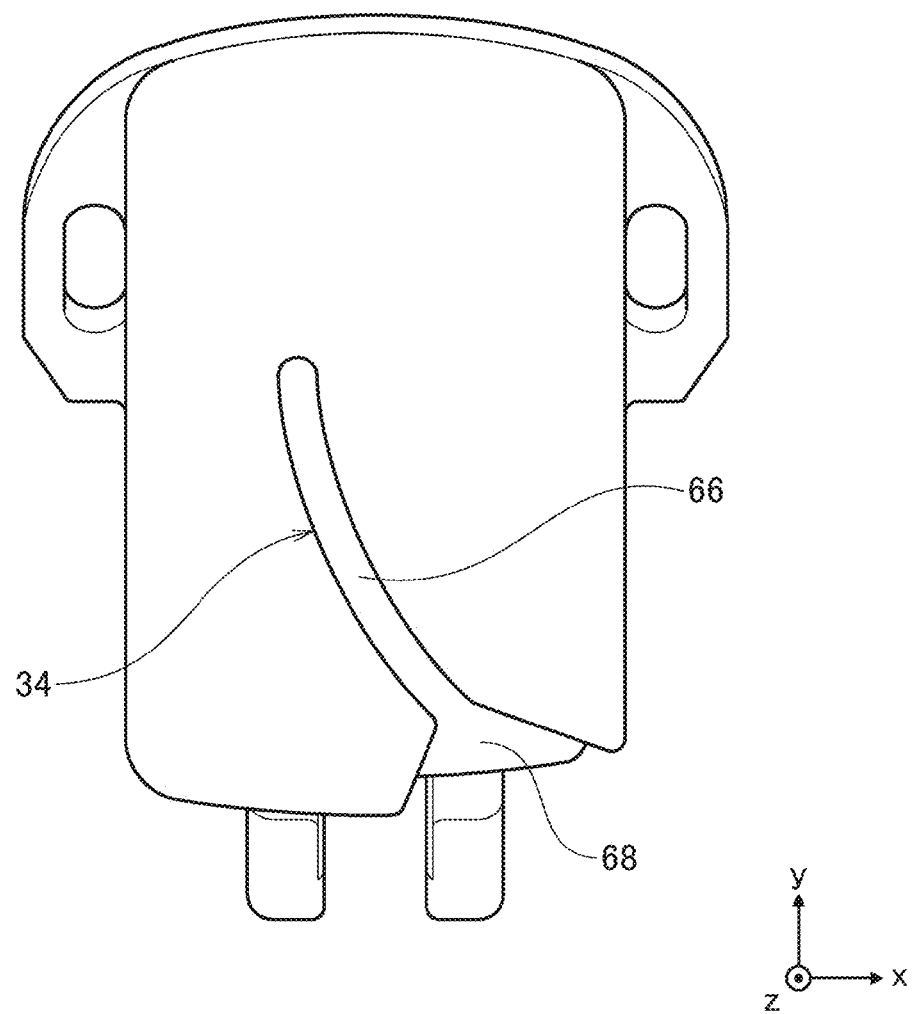
FIG. 6 is a view illustrating a groove of an upper link according to the embodiment.

FIG. 6 is a view illustrating the groove 34 of the upper link 16 according to the embodiment. FIG. 6 is a bottom view of the upper link 16 at a bending angle of 0°. The groove 34 is formed on a surface opposite to the thigh connector 32 and includes a curved portion 66 and an introducing portion 68 into which the protrusion 58 of the driven member 38 fits. The curved portion 66 is curved from the vicinity of the center of the bottom surface of the upper link 16 while extending backward to the right. The introducing portion 68 is formed so as to communicate with the curved portion 66 and to have a wider width toward the posterior end. As illustrated in FIG. 3C, when the bending angle of the knee unit 10 increases, the protrusion 58 comes off the groove 34. When returning from this state to the state illustrated in FIG. 3A and FIG. 3B, the introducing portion 68 leads the protrusion 58 to the curved portion 66.

Figure 7A:
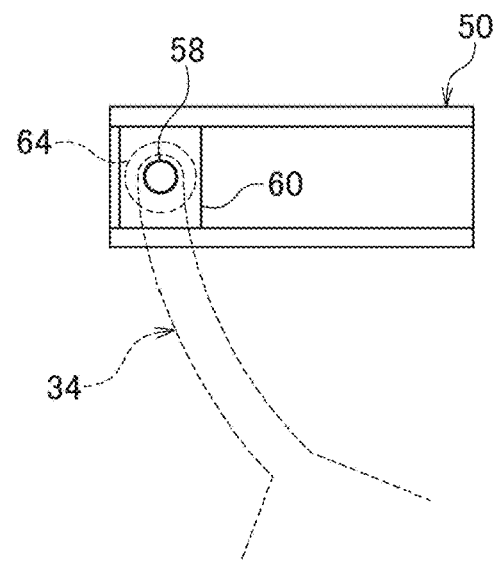
FIG. 7A to FIG. 7C are views illustrating how a driven member moves as a knee unit according to the embodiment is bent.
Figure 7B:
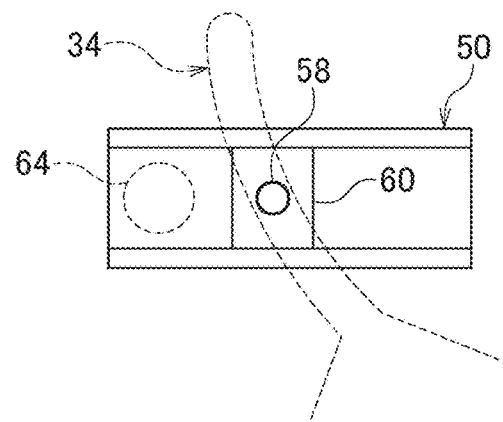
Figure 7C:
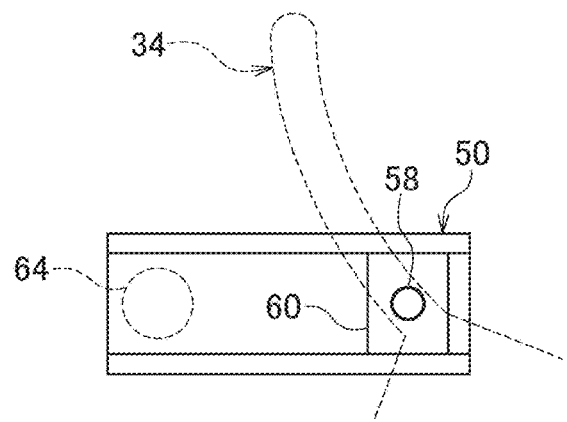
Figure 8:
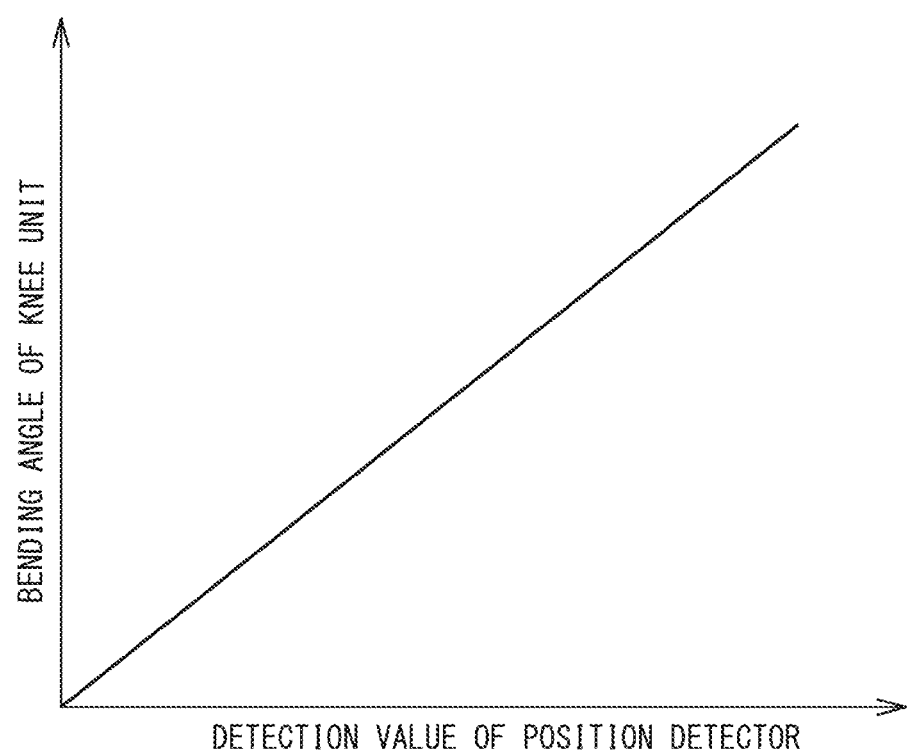
FIG. 8 is a graph illustrating a relationship between the detection value of a position detector and the bending angle of the knee unit according to the embodiment.

FIG. 7A to FIG. 7C are views illustrating how the driven member 38 moves in accordance with the rotation of the knee unit 10 according to the embodiment. FIG. 7A to FIG. 7C are views illustrating cases where the bending angles of the knee unit 10 are 0°, 45°, and 90°, respectively. When the knee unit 10 is bent, the protrusion 58 is pushed by the groove 34, and the driven member 38 moves. When the driven member 38 moves, the distance between the magnet 62 and the position detector 64 changes, and the detection value of the position detector 64 changes. FIG. 8 is a graph illustrating the relationship between the detection value of the position detector 64 and the bending angle of the knee unit 10. The angle detector 42 obtains the detection value of the position detector 64 and obtains the bending angle of the knee unit 10 from the relationship illustrated in FIG. 8.

Figure 9:
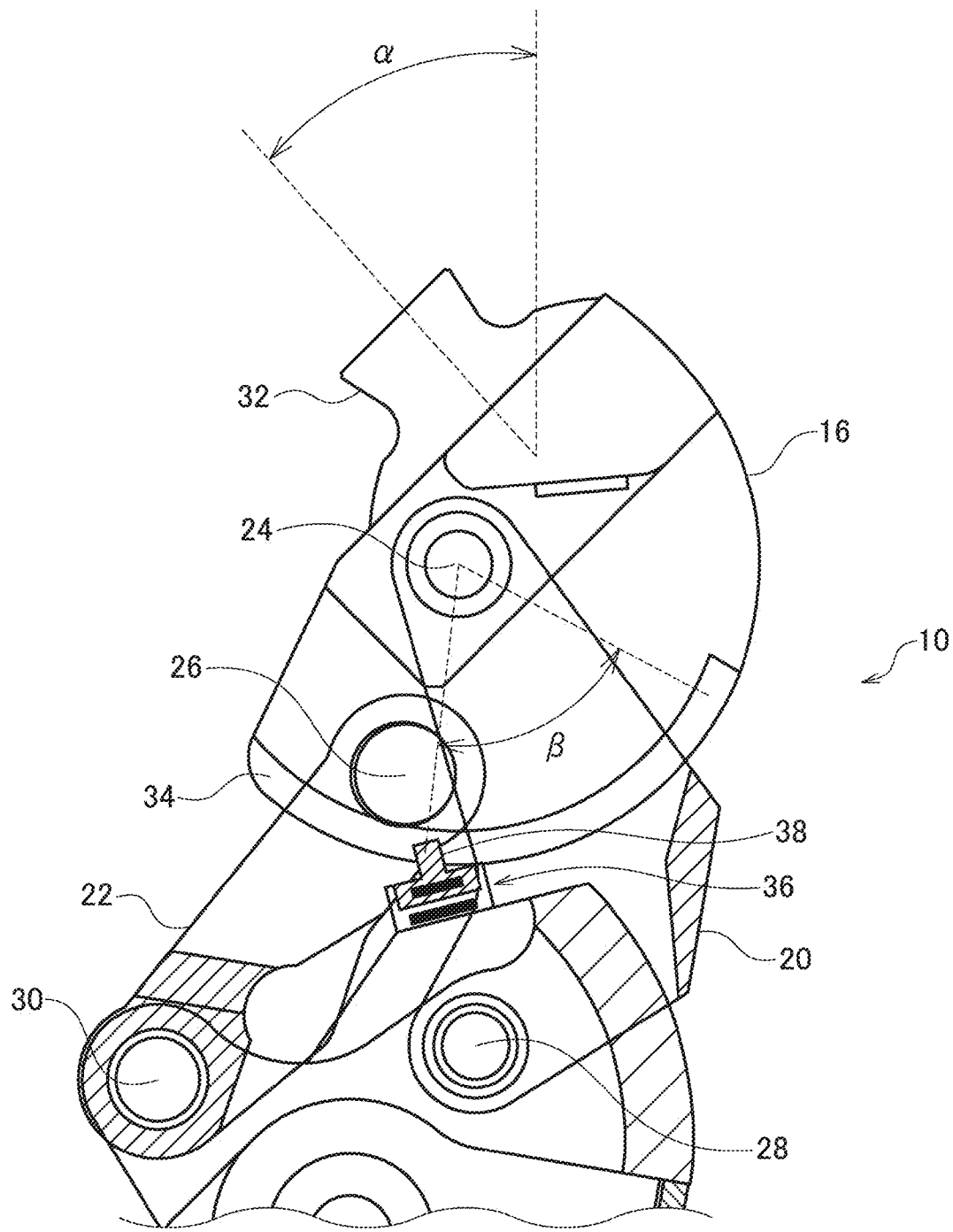
FIG. 9 is a view illustrating a bending angle of the knee unit and a moving angle of the driven member according to the embodiment.
Figure 10A:
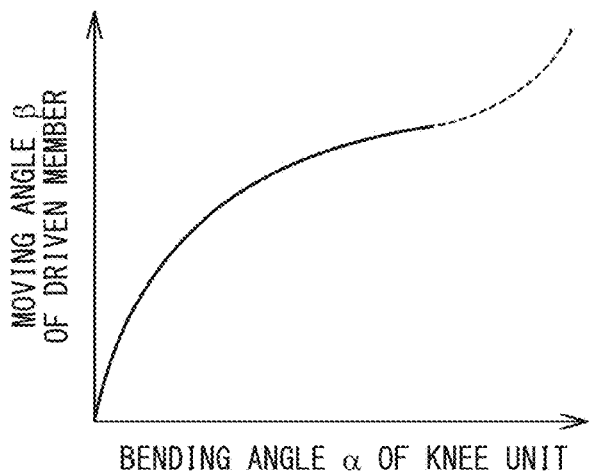
FIG. 10A to FIG. 10C are graphs illustrating the relationship among the bending angle of the knee unit, the moving angle of the driven member, and the axial direction moving amount of the driven member according to the embodiment.

Here, as illustrated in FIG. 9, let the bending angle of the knee unit 10 be α, and let the moving angle of the driven member 38 in the circumferential direction about the first shaft 24 be β. Since the upper link 16 rotates while moving backward, the relationship between the bending angle α of the knee unit 10 and the moving angle β of the driven member 38 is not linear but is represented by a curve having an inflection point at a boundary between a solid line portion and a broken line portion as illustrated in FIG. 10A. The moving angle β is expressed by the following expression (1) as a function using the bending angle α.

$$\beta = f(\alpha) \tag{1}$$

The curved portion 66 of the groove 34 is formed such that the moving amount X of the driven member 38 satisfies the following equation (2). The relationship between the moving amount X of the driven member 38 and the bending angle α of the knee unit 10 in this case is illustrated in FIG. 10B.

$$X = a \cdot f^{-1}(\beta) \tag{2}$$

The function $f^{-1}(\beta)$ is the inverse function of $f(\beta)$. The symbol "a" is a coefficient and is set to a desired value. When the coefficient a is smaller, the moving amount X of the driven member 38 relative to the bending angle α of the knee unit 10 becomes smaller. By reducing the moving amount X, the change amount of the magnetic field can be detected more accurately even with limited magnetic force. The coefficient a is set in accordance with dimensions of the respective parts of the knee unit 10. Although the case of using the inverse function has been described, other methods such as the least squares method may be used.

Figure 10B:
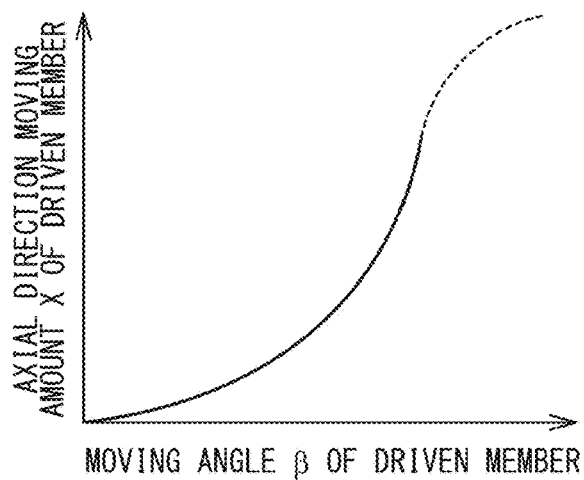
Figure 10C:
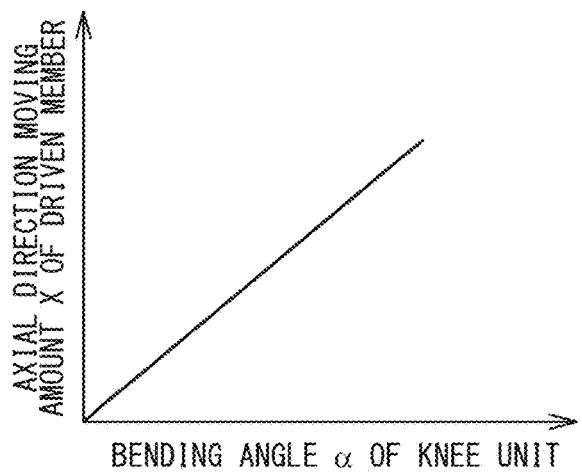

In the case where the curved portion 66 of the groove 34 is formed such that equation (2) is satisfied in the regions indicated by the solid line ins FIG. 10A and FIG. 10B, the relationship between the bending angle α of the knee unit 10 and the moving amount X of the driven member 38 becomes linear as illustrated in FIG. 10C. As a result, the relationship illustrated in FIG. 8 is obtained. By allowing the relationship between the output value of the position detector and the bending angle α of the knee unit 10 to be linear, calculation processing of the bending angle α can be simplified. In the present embodiment, in the relationship illustrated in FIG. 10A, the groove 34 is formed such that up to the angle at the inflection point is covered by the detection range of the bending angle α of the knee unit 10; however, the groove 34 may be formed such that angles exceeding the inflection point are covered by the detection range. In this case, an inflection point is also formed in the curved portion 66 of the groove 34. As a result, the detection range of the bending angle α of the knee unit 10 can be expanded. In the case where a range up to the inflection point is set as the detection range as in the present embodiment, the shape of the curved portion 66 of the groove 34 can be simplified to reduce the influence of assembly errors, which enables accurate detection of the bending angle of the knee unit 10.

The usage and operation according to the above configuration are as follows. The multi-articulated link knee joint 100 is used while the thigh connector 32 is connected to a socket attached to the thigh of the user with the leg part connected to the leg connector 40. The knee unit 10 bends when the upper link 16 rotates with respect to the lower link 18 by the multi-articulated link mechanism. When the knee unit 10 is bent, the angle detector 42 obtains the bending angle from the detection value of the position detector 64.

The controller 44 controls the auxiliary driver 46 in accordance with the bending angle to assist the motion of the knee unit 10. The groove 34 for detecting the bending angle, the rotation detector 36 including the driven member 38 and the position detector 64 are included in the knee unit 10, which enables compatibility with auxiliary drivers of different types to allow detection of the bending angle of the knee unit 10. In deploying various product groups, the configuration for detecting the bending angle can be shared to reduce the manufacturing cost.

Moreover, according to the multi-articulated link knee joint 100 according to the present embodiment, the position detector 64 and the angle detector 42 (that is, control device 14) are provided at the same link member, that is, the lower link member. Since the angle detector 42 obtains the bending angle of the knee unit 10 from the detection result of the rotation detector 36, in order to transmit detection information of the position detector 64 to the angle detector 42, it is necessary that the position detector 64 and the angle detector 42 be connected by wiring. In the case where the position detector 64 and the angle detector 42 are provided at separate link members, since there is a movable portion in the middle of the wiring, it is necessary to adopt a structure that does not cause a failure in the wiring such as disconnection. This is not preferable since this leads to an increase in the size and the cost of the knee joint. On the other hand, in the multi-articulated link knee joint 100 according to the present embodiment, since the position detector 64 and the angle detector 42 are provided at the same lower link member, there is no movable portion in the middle of the wiring, and thus the wiring can be simplified. This results in downsizing and cost reduction of the knee joint.

Hereinafter, variations of the above embodiment will be described.

First Variation

Figure 11:
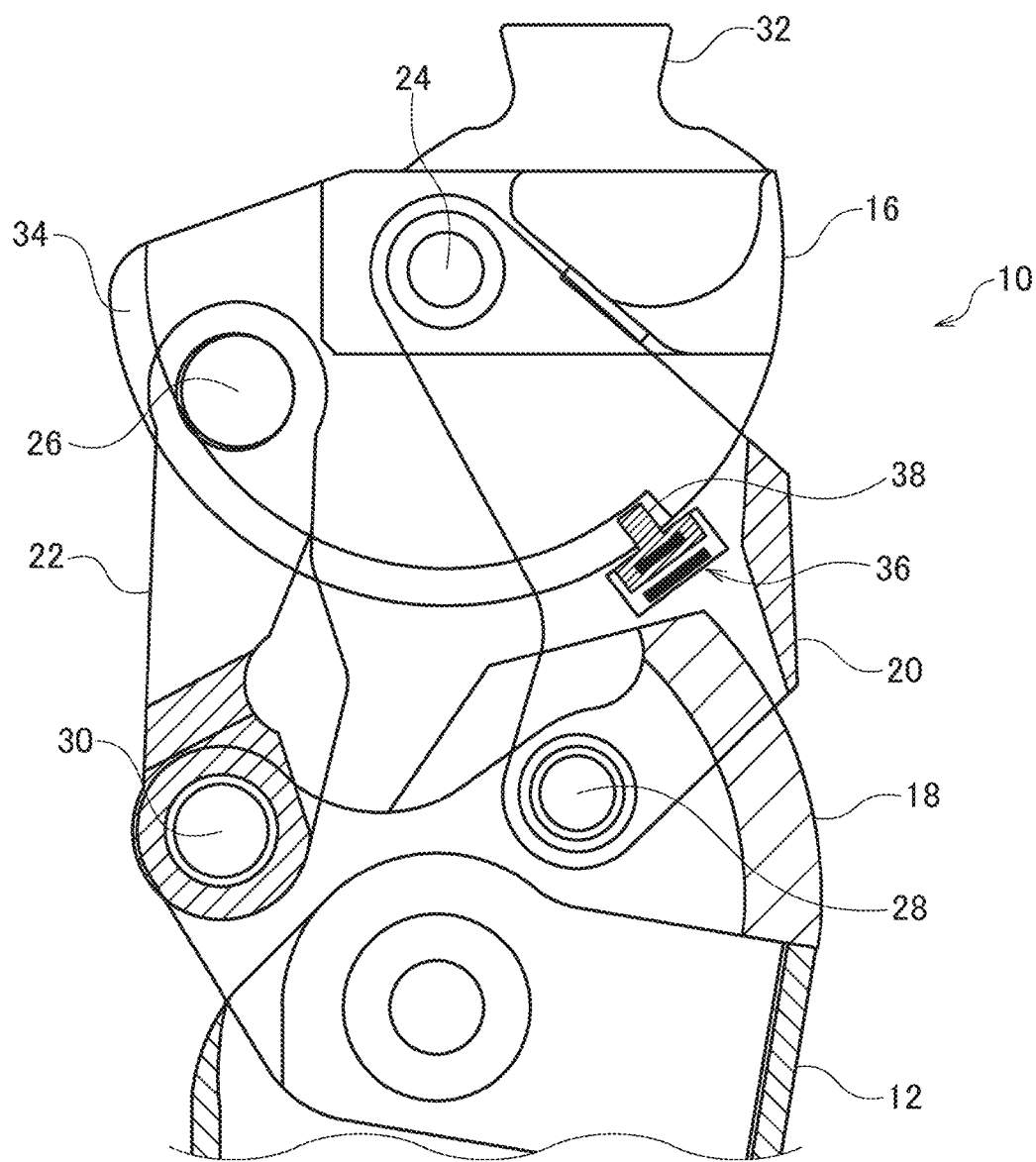
FIG. 11 is a schematic cross-sectional view illustrating a multi-articulated link knee joint according to a first variation.

FIG. 11 is a schematic cross-sectional view illustrating a multi-articulated link knee joint 102 according to a first variation. The multi-articulated link knee joint 102 is different from the embodiment in that a rotation detector 36 is provided at an anterior link 20, and a groove 34 is formed in a linear shape inclined with respect to the rotation direction of an upper link 16.

Figure 12A:
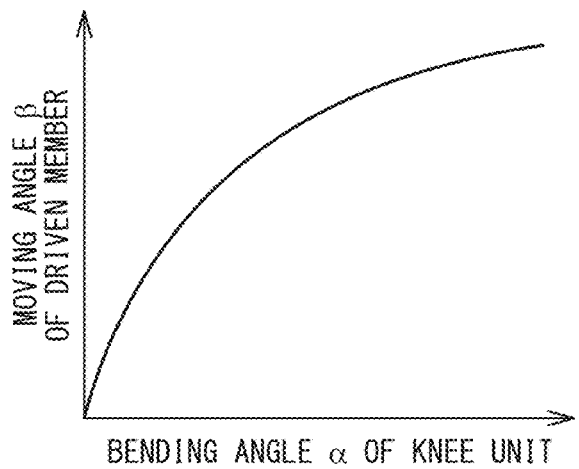
FIG. 12A to FIG. 12C are graphs illustrating the relationship among the bending angle of a knee unit, the moving angle of a driven member, and the axial direction moving amount of the driven member according to the first variation.
Figure 12B:
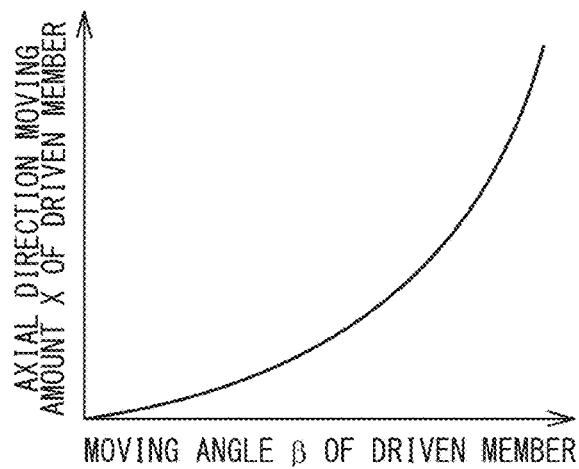
Figure 12C:
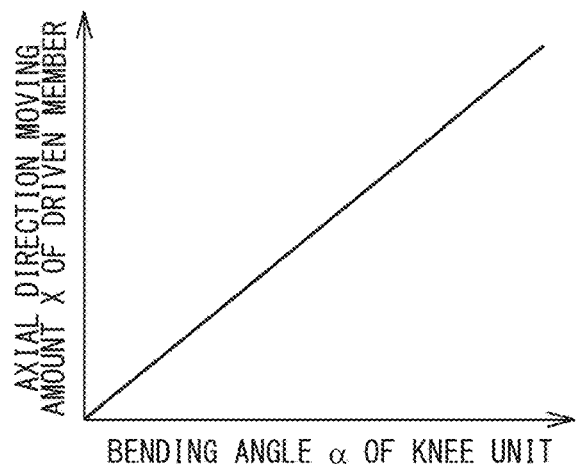

FIG. 12A to FIG. 12C are graphs illustrating the relationship among the bending angle α of a knee unit 10, the moving angle β of a driven member 38, and the axial direction moving amount X of the driven member 38 according to the first variation. Like in the embodiment, the groove 34 is formed such that the relationship between the bending angle α of the knee unit 10 and the moving amount X of the driven member 38 is linear. In the case where the rotation detector 36 is provided at the anterior link 20, no inflection point appears in the relationship between the bending angle α and the moving angle β. As a result, the detection range of the bending angle α of the knee unit 10 can be expanded while the shape of the curved portion 66 of the groove 34 is maintained simple.

Second Variation

Figure 13:
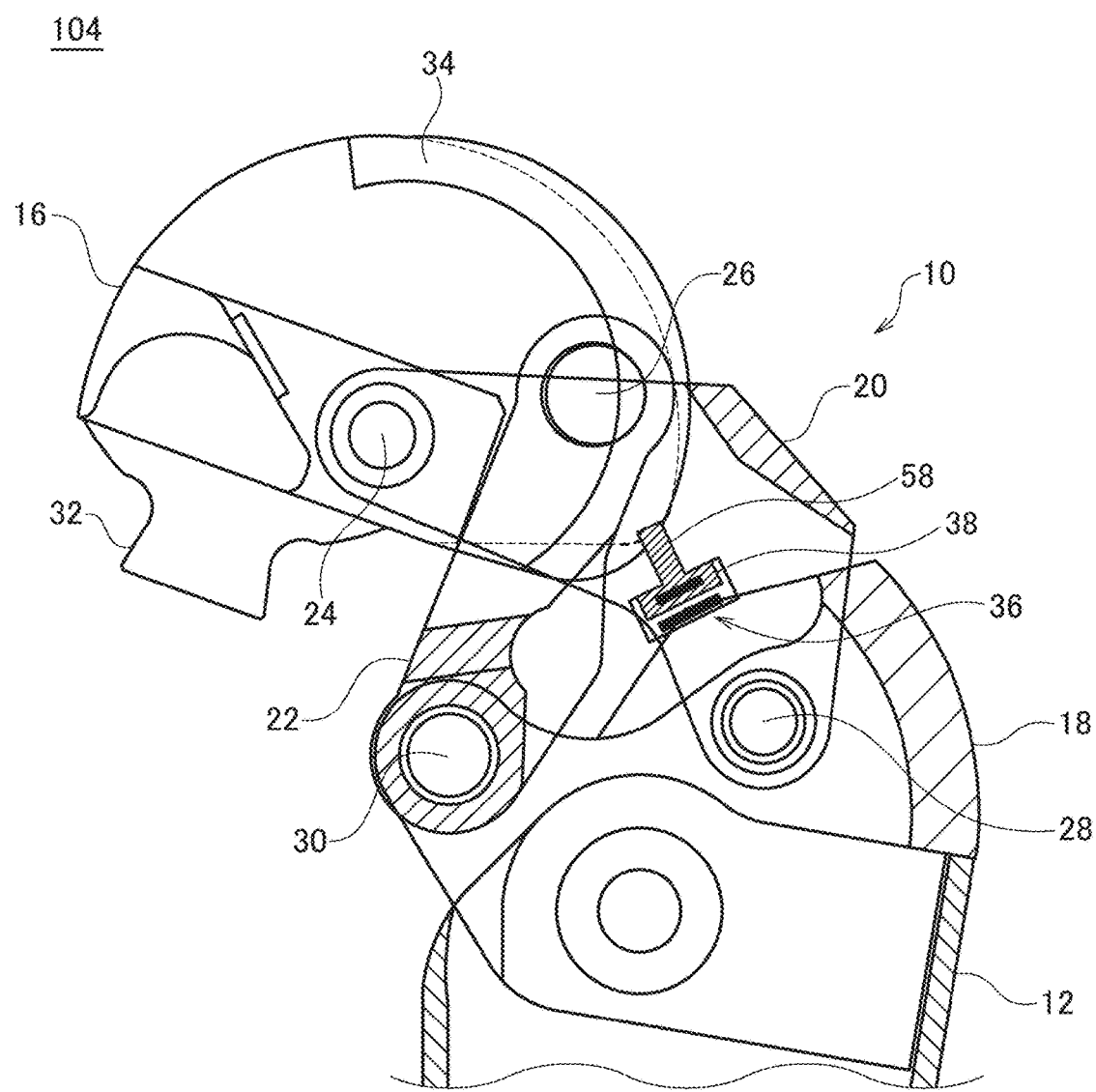
FIG. 13 is a schematic cross-sectional view illustrating a multi-articulated link knee joint according to a second variation.

FIG. 13 is a schematic cross-sectional view illustrating a multi-articulated link knee joint 104 according to a second variation. In the multi-articulated link knee joint 104, an upper link 16 is larger than that of the embodiment indicated by a broken line, and a protrusion 58 of a driven member 38 is longer than that of the embodiment. Furthermore, no introducing portion 68 is formed in a groove 34, and the groove 34 is formed with the same width from the anterior side to the posterior side. The detection range of the bending angle can be expanded by adopting a configuration in which the protrusion 58 does not come off the groove 34 even when the knee unit 10 is greatly bent.

Other Variations

In the configuration in which the groove 34 is formed in the upper link 16, the rotation detector 36 may be provided at the posterior link 22. The groove 34 may be provided at the lower link 18 with the rotation detector 36 provided at the upper link 16. Moreover, the driven member 38 and the position detector 64 may be provided at different links. Note that, by providing the position detector 64 at the lower link 18, the wiring between the position detector 64 and the control device 14 accommodated in the lower leg part 12 can be simplified. According to this configuration, the knee unit 10 can be downsized. The control device 14 and the position detector 64 may be provided at the upper link 16. Also in this case, wiring between the position detector 64 and the control device 14 can be simplified.

The driven member 38 may be secured to the upper link 16 or may be a part of the upper link 16. In this case, the lower link 18 is provided with the position detector 64 for detecting a change in the position of the driven member 38. The position of the driven member 38 rotating in conjunction with the upper link 16 is detected, and the bending angle of the knee unit 10 can be obtained from this detection result. With this configuration, the groove 34 is no longer required to be formed as the moving mechanism, and thus the structure can be simplified. Meanwhile, in the case where the moving mechanism is included, the moving amount of the driven member 38 can be reduced, and the rotation detector 36 can be downsized as compared with the structure without the moving mechanism.

Although the groove 34 is formed as the moving mechanism for moving the driven member 38 in the embodiment; however, the moving mechanism is not limited thereto. As a moving mechanism, a protrusion may be provided instead of the groove 34, and a groove to be fitted into the protrusion may be formed in a driven member 38. Alternatively, as a moving mechanism, a wall projecting from the outer circumferential surface of the upper link 16 and extending in the circumferential direction may be formed to allow the wall to push the protrusion 58 to move the driven member 38.

Furthermore, although the magnet 62 is provided at the driven member 38 and the position of the driven member 38 is detected by the Hall element in the embodiment, the position detector 64 is not limited to a Hall element. The position of the driven member 38 may be detected using a capacitance type proximity sensor, an infrared sensor, or an optical sensor as the position detector 64.

In the embodiment, the knee unit 10 is bent by the four-articulated link mechanism; however, the structure of the knee unit 10 is not limited to this as long as the structure is a multi-articulated link mechanism.

Figure 14:
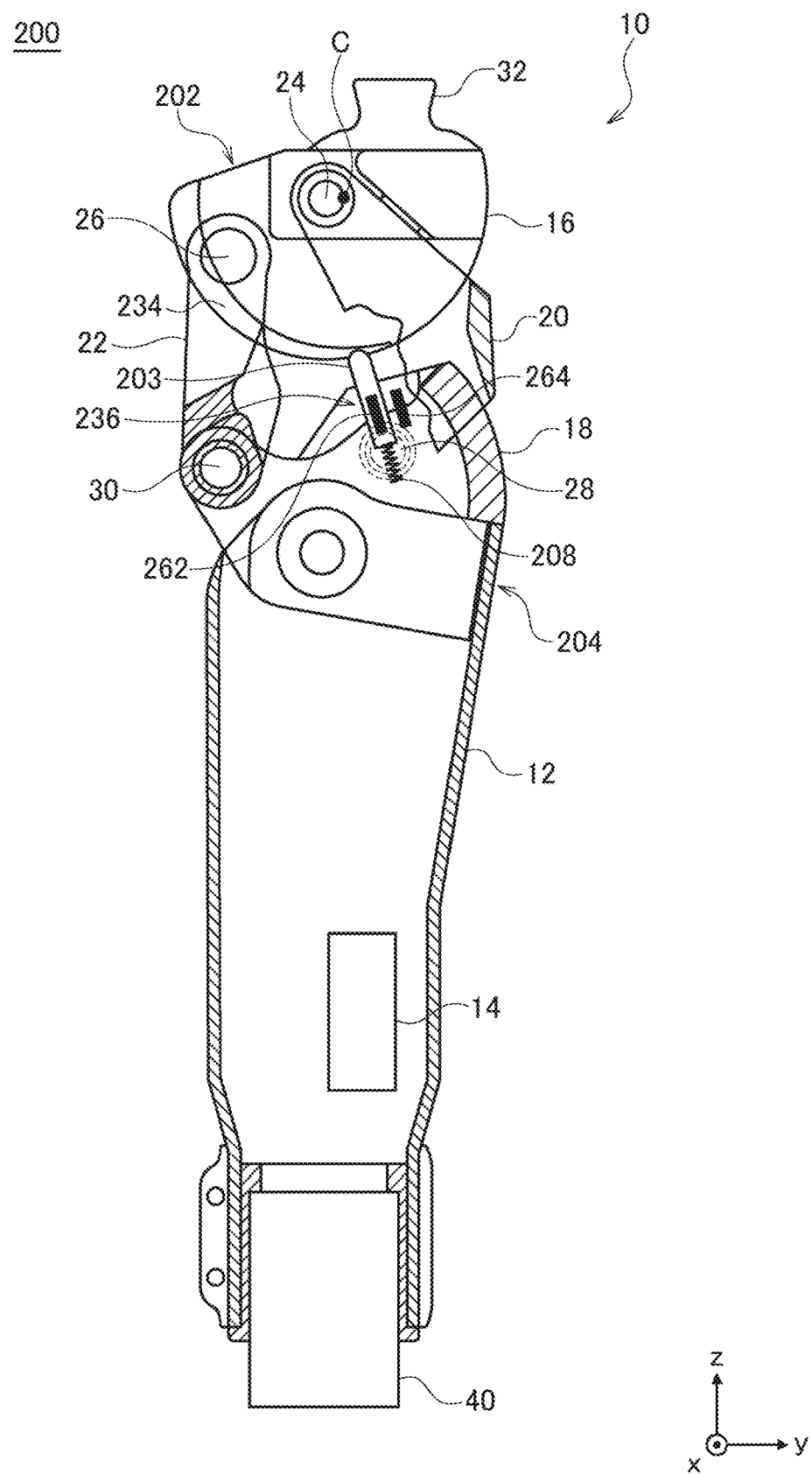
FIG. 14 is a schematic cross-sectional view of a multi-articulated link knee joint according to another embodiment.
Figure 15:
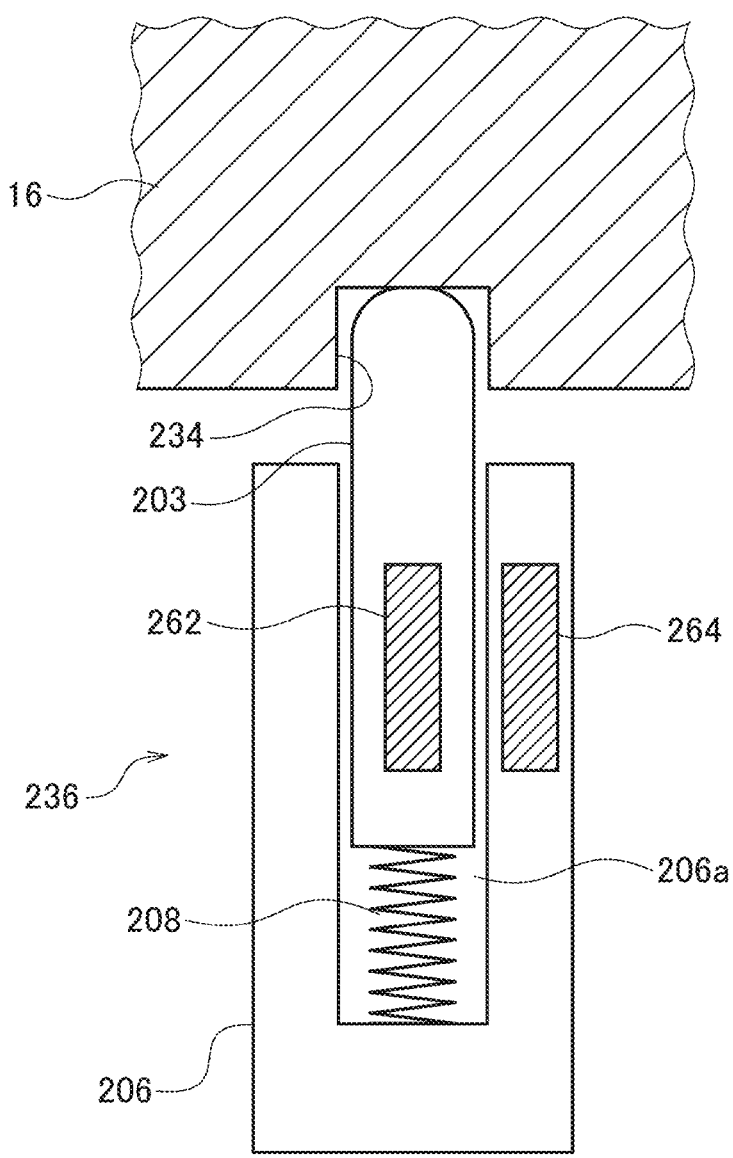
FIG. 15 is a schematic diagram illustrating a rotation detector according to the other embodiment when the bending angle of a knee unit is 0°.

FIG. 14 is a schematic cross-sectional view of a multi-articulated link knee joint 200 according to another embodiment. The bending angle of a knee unit 10 illustrated in FIG. 14 is 0°. In the multi-articulated link knee joint 200, the structure of a rotation detector 236 is different from that of the multi-articulated link knee joint 100 described above. FIG. 15 is a schematic diagram illustrating the rotation detector 236 when the bending angle of the knee unit 10 is 0°. Note that illustration of an auxiliary driver is omitted also in the drawings illustrating the present embodiment.

The rotation detector 236 includes an abutting member 203, a case 206, a spring 208, a magnet 262, and a position detector 264.

The case 206 has an accommodating space 206a open upward. The case 206 is secured to a lower link 18. The abutting member 203 and the spring 208 are accommodated in the accommodating space 206a of the case 206. The spring 208 energizes the abutting member 203 such that the upper portion of the abutting member 203 protrudes from the accommodating space 206a. The magnet 262 is attached to the abutting member 203. The position detector 264 includes a Hall element and outputs a detection value corresponding to the distance to the magnet 262.

Figure 16:
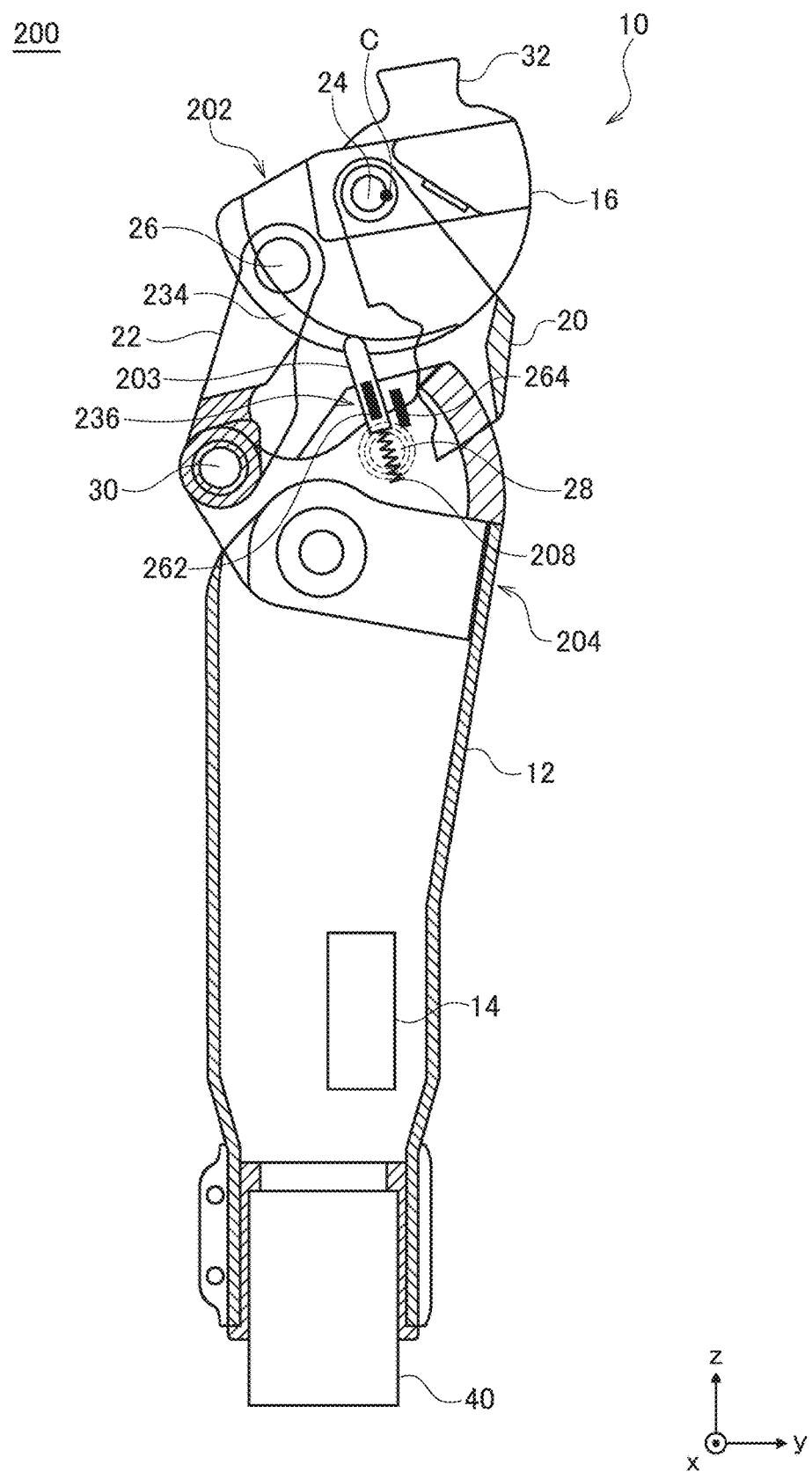
FIG. 16 is a schematic cross-sectional view of the multi-articulated link knee joint according to the other embodiment when the bending angle of the knee unit is large.

A groove 234 extending in an arc-shape in the rotation direction of an upper link 16 is formed on the outer circumferential surface of the upper link 16 on the lower link 18 side. The groove 234 is formed such that the depth varies along the extending direction. In FIG. 16, symbol "C" indicates the center of the groove 234 extending in an arc shape. As illustrated in FIG. 16, the center C of the groove 234 is eccentric anteriorly with respect to the center of the outer circumferential surface of the upper link 16 on the lower link 18 side (the center of a first shaft 24). With this structure, when the bending angle of the knee unit 10 is 0°, the depth of the groove 234 increases as it extends posteriorly. The rotation detector 236 is attached to the lower link 18 such that the upper portion of the abutting member 203 fits into the groove 234. The abutting member 203 is energized by the spring 208 and abuts against the bottom of the groove 234.

Figure 17:
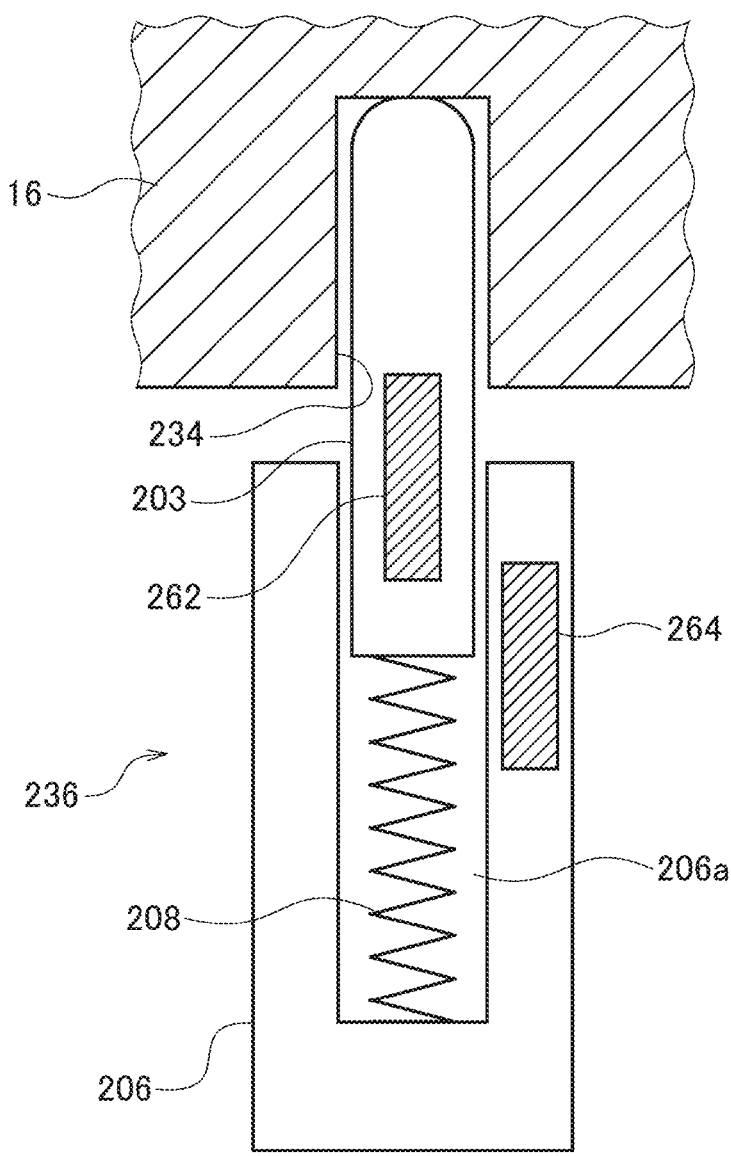
FIG. 17 is a schematic diagram illustrating the rotation detector according to the other embodiment when the bending angle of the knee unit is large.

FIG. 16 is a schematic cross-sectional view illustrating the multi-articulated link knee joint 200 when the bending angle of the knee unit 10 is greater. FIG. 17 is a schematic diagram illustrating the rotation detector 236 when the bending angle of the knee unit 10 is greater.

In the present embodiment, the abutting member 203 corresponds to the driven member that moves in accordance with the rotation of the upper link member 202. As illustrated in FIG. 16 and FIG. 17, as the bending angle of the knee unit 10 increases, the depth of the groove 234 into which the abutting member 203 of the rotation detector 236 is fitted increases. Since the abutting member 203 is energized by the spring 208 so as to abut against the bottom of the groove 234, when the depth of the groove 234 increases, the abutting member 203 moves in a direction of protruding from the case 206.

Due to the movement of the abutting member 203, the distance between the magnet 262 attached to the abutting member 203 and the position detector 264 attached to the case 206 changes. The position detector 264 outputs a detection value corresponding to the position of the abutting member 203, that is, the bending angle of the knee unit 10. The angle detector 42 (see FIG. 4) of the control device 14 obtains the bending angle from the detection value of the position detector 64. For example, when a table is generated in advance by measuring the relationship between the bending angle of the knee unit 10 and the detection value of the position detector 264, a bending angle of the knee unit 10 can be obtained from a detection value of the position detector 264 by referring to the table. The controller 44 (see FIG. 4) controls the auxiliary driver 46 (see FIG. 4) in accordance with the bending angle to assist the motion of the knee unit 10.

Also in the multi-articulated link knee joint 200 according to the present embodiment, the structure for detecting the bending angle is provided at the knee unit 10. That is, the groove 34 is formed in the upper link 16, and the rotation detector 236 including the abutting member 203 and the position detector 264 is provided at the lower link 18. This enables compatibility with auxiliary drivers of different types to allow detection of the bending angle of the knee unit 10. In deploying various product groups, the configuration for detecting the bending angle can be shared to reduce the manufacturing cost.

Moreover, according to the multi-articulated link knee joint 200 of to the present embodiment as well, the position detector 264 and the angle detector 42 (control device 14) are provided at the same link member, that is, at the lower link member 204, and thus the wiring can be simplified. Note that the position detector and the angle detector may be provided at another link member such as the upper link member.

The magnet 262 is provided at the abutting member 203 and the position of the abutting member 203 is detected by the Hall element in the present embodiment; however, the position detector 264 is not limited to a Hall element. The position of the abutting member 203 may be detected using a capacitance type proximity sensor, an infrared sensor, or an optical sensor as the position detector 264.

Figure 18:
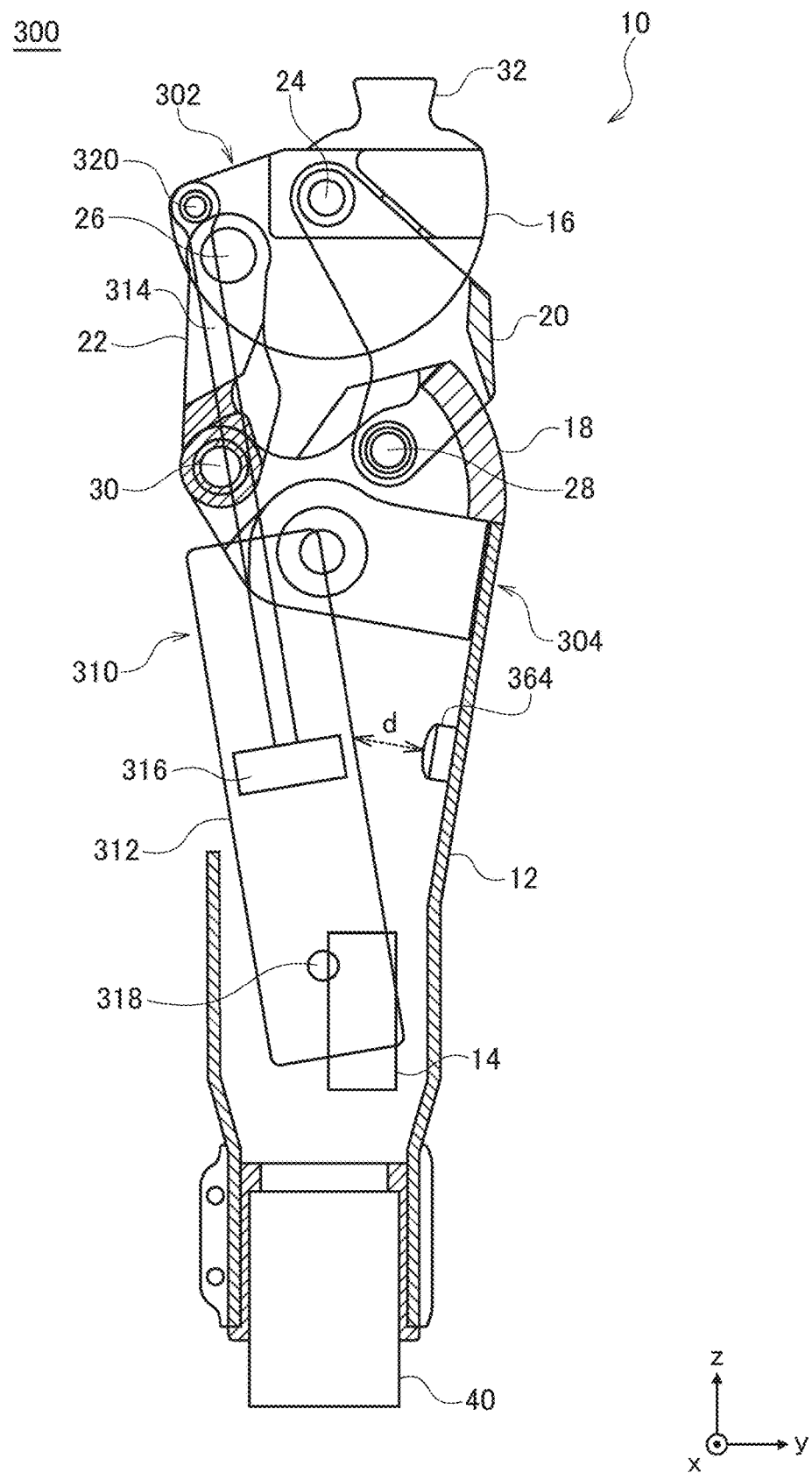
FIG. 18 is a schematic cross-sectional view of a multi-articulated link knee joint according to still another embodiment.
Figure 19:
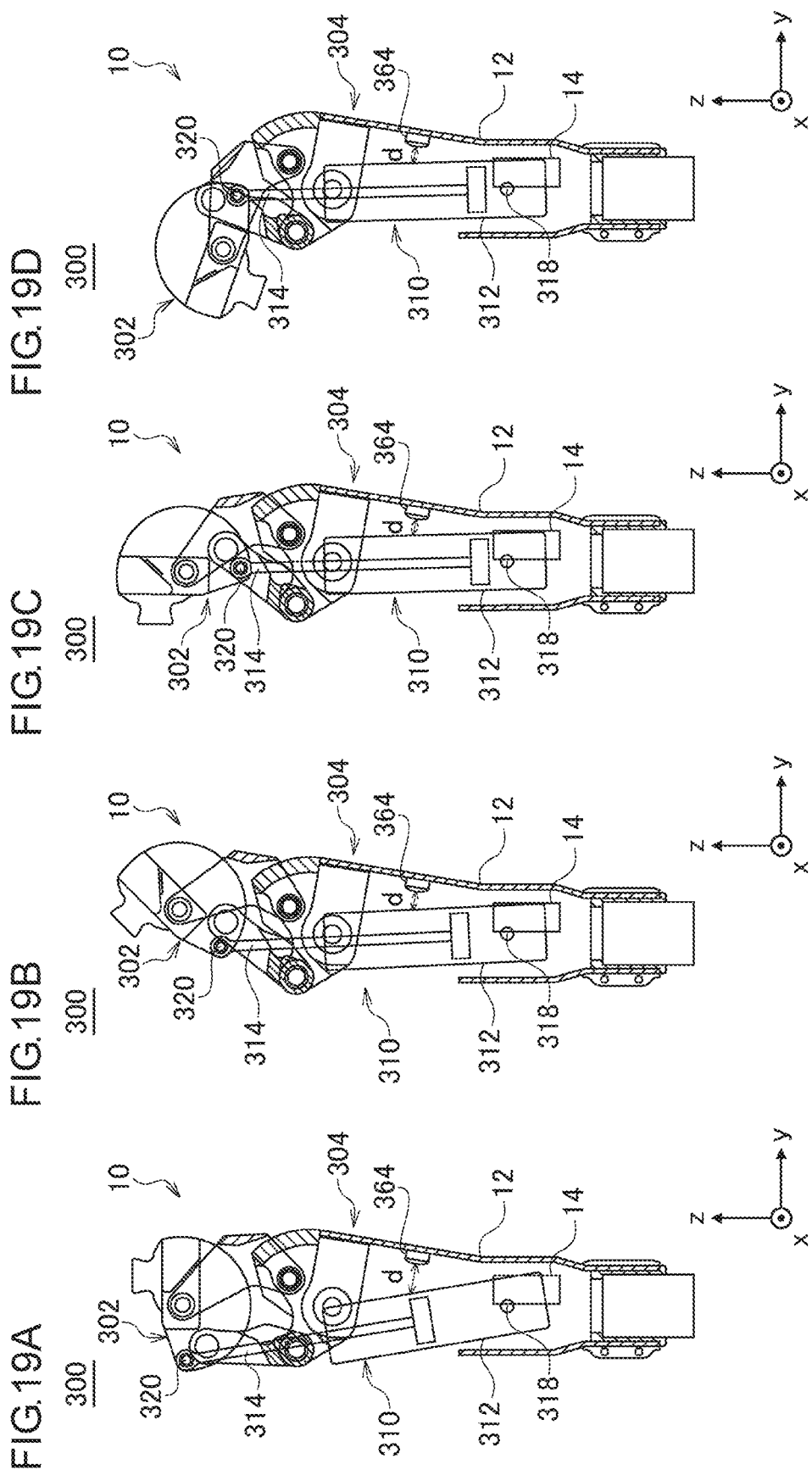
FIG. 19A to FIG. 19D are diagrams illustrating how a knee unit is bent.

FIG. 18 is a schematic cross-sectional view of a multi-articulated link knee joint 300 according to still another embodiment. The bending angle of the knee unit 10 illustrated in FIG. 18 is 0°. As illustrated in FIG. 18, the multi-articulated link knee joint 300 according to the present embodiment includes a cylinder device 310 as an auxiliary driver for assisting the motion of a knee unit 10. The cylinder device 310 may be an air cylinder or a hydraulic cylinder.

The cylinder device 310 includes a cylinder tube 312, a piston rod 314 movable relative to the cylinder tube 312, and a piston 316 movably accommodated in the cylinder tube 312 and secured to the piston rod 314.

The cylinder device 310 is provided so as to couple an upper link member 302 and a lower link member 304. That is, the cylinder tube 312 is rotatably supported by a lower shaft 318 provided at a lower leg part 12 of the lower link member 304, and the piston rod 314 is rotatably supported by an upper shaft 320 provided at an upper link 16 of the upper link member 302. The cylinder device 310 provided in this manner swings about the lower shaft 318 in accordance with the rotation of the upper link member 302.

In addition, in the multi-articulated link knee joint 300 according to the present embodiment, a position detector 364 is provided at the lower leg part 12 of the lower link member 304. As illustrated in FIG. 18, the position detector 364 is installed in the lower leg part 12 to measure the distance d from the lower leg part 12 to the cylinder device 310 (more specifically, distance from the lower leg part 12 to the cylinder tube 312). The position detector 364 is not particularly limited as long as the distance d to the cylinder device 310 can be detected, and for example an infrared sensor can be used.

FIG. 19A to FIG. 19D are diagrams illustrating how the knee unit 10 is bent. The bending angles of the knee unit 10 illustrated in FIG. 19A to FIG. 19D are 0°, 45°, 90°, and 160°, respectively.

In the present embodiment, the cylinder device 310 corresponds to the driven member that moves in accordance with the rotation of the upper link member 202. As illustrated in FIG. 19A to FIG. 19D, the distance d from the lower leg part 12 to the cylinder device 310 changes in accordance with a change in the bending angle of the knee unit 10. In the multi-articulated link knee joint 300 according to the present embodiment, as the bending angle of the knee unit 10 increases, the distance d from the lower leg part 12 to the cylinder device 310 decreases.

An angle detector 42 (see FIG. 4) of a control device 14 obtains the bending angle from the detection value of the position detector 364. For example, when a table is generated in advance by measuring the relationship between the bending angle of the knee unit 10 and the detection value of the position detector 364, a bending angle of the knee unit 10 can be obtained from a detection value of the position detector 364 by referring to the table. The controller 44 (see FIG. 4) controls the cylinder device 310 in accordance with the bending angle to assist the motion of the knee unit 10.

As described above, in the multi-articulated link knee joint 300 according to the present embodiment, the position detector 364 is provided at the lower link member 304 (more specifically, the lower leg part 12) to measure the distance d from the lower link member 304 (more specifically, the lower leg part 12) to the cylinder device 310 to obtain the bending angle of the knee unit 10 on the basis of this distance d. Therefore, it is not necessary to use a special device having a magnet or a magnetic sensor therein as the cylinder device 310. That is, this enables compatibility with a generic cylinder device 310 and allows the bending angle of the knee unit 10 to be detected.

Moreover, according to the multi-articulated link knee joint 300 of to the present embodiment as well, the position detector 364 and the angle detector 42 (control device 14) are provided at the same link member, that is, at the lower link member 304, and thus the wiring can be simplified. Note that the position detector and the angle detector may be provided at another link member such as the upper link member.

Figure 20:
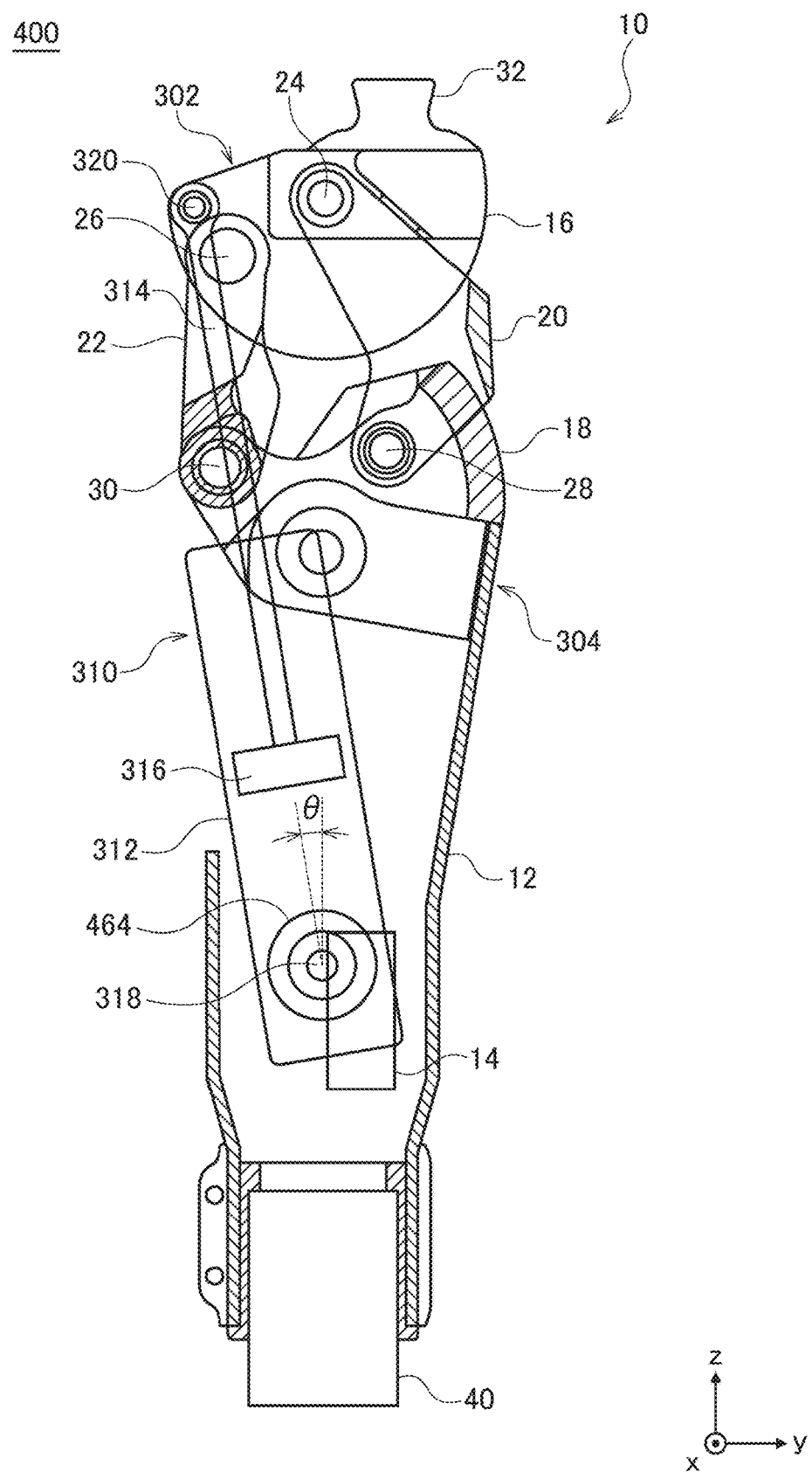
FIG. 20 is a schematic cross-sectional view of a multi-articulated link knee joint according to yet another embodiment.

FIG. 20 is a schematic cross-sectional view of a multi-articulated link knee joint 400 according to yet another embodiment. The bending angle of a knee unit 10 illustrated in FIG. 20 is 0°. As illustrated in FIG. 20, a multi-articulated link knee joint 400 according to the present embodiment is different from the multi-articulated link knee joint 300 described above (see FIG. 19A to FIG. 19D) in that a position detector 464 is structured and arranged to detect the inclination angle θ of a cylinder device 310 with respect to a lower link member 304. In this example, the angle formed by the longitudinal direction of a cylinder device 310 (in other words, expansion/contraction direction of a piston rod 314) and the z axis is regarded as the inclination angle θ of the cylinder device 310.

The position detector 464 is attached to a lower shaft 318 of a lower leg part 12. As the position detector 464, for example, a potentiometer, a rotary encoder, a resolver, or the like can be used.

In the present embodiment as well, the cylinder device 310 corresponds to the driven member that moves in accordance with the rotation of the upper link member 202. FIG. 21A to FIG. 21D are diagrams illustrating how the knee unit 10 is bent. The bending angles of the knee unit 10 illustrated in FIG. 21A to FIG. 21D are 0°, 45°, 90°, and 160°, respectively. As illustrated in FIG. 21A to FIG. 21D, the inclination angle θ of the cylinder device 310 with respect to the lower leg part 12 changes in accordance with a change in the bending angle of the knee unit 10. In the multi-articulated link knee joint 300 according to the present embodiment, as the bending angle of the knee unit 10 increases, the inclination angle θ of the cylinder device 310 with respect to the lower leg part 12 decreases.

The angle detector 42 (see FIG. 4) of the control device 14 obtains the bending angle from the detection value of the position detector 464. For example, when a table is generated in advance by measuring the relationship between the bending angle of the knee unit 10 and the detection value of the position detector 464, a bending angle of the knee unit 10 can be obtained from a detection value of the position detector 464 by referring to the table. The controller 44 (see FIG. 4) controls the cylinder device 310 in accordance with the bending angle to assist the motion of the knee unit 10.

As described above, in the multi-articulated link knee joint 400 according to the present embodiment, the position detector 464 is provided at the lower link member 304 (more specifically, the lower leg part 12) to measure the inclination angle θ of the cylinder device 310 with respect to the lower link member 304 (more specifically, the lower leg part 12) to obtain the bending angle of the knee unit 10 on the basis of the inclination angle θ. Therefore, it is not necessary to use a special device having a magnet or a magnetic sensor therein as the cylinder device 310. That is, this enables compatibility with a generic cylinder device 310 and allows the bending angle of the knee unit 10 to be detected.

Moreover, according to the multi-articulated link knee joint 400 of to the present embodiment as well, the position detector 464 and the angle detector 42 (control device 14) are provided at the same link member, that is, at the lower link member 304, and thus the wiring can be simplified. Note that the position detector and the angle detector may be provided at another link member such as the upper link member.

The present invention has been described above on the basis of the embodiments. The embodiments are merely examples, and thus it should be understood by a person skilled in the art that combinations of components or processing processes of the examples may include various variations and that such variations are also within the scope of the present invention.

What is claimed is:

1. A multi-articulated link knee joint comprising:
   a knee unit in which an upper link member is structured to rotate relative to a lower link member by a multi-articulated link mechanism including a plurality of link members including the upper link member and the lower link member;
   a driven member structured to move in accordance with rotation of the upper link member;
   a position detector structured to detect a position of the driven member, the position detector provided at one of the plurality of link members;
   an angle detector structured to obtain a bending angle of the knee unit from the position of the driven member; and
   a moving mechanism structured to move the driven member in accordance with rotation of the upper link member,
   wherein the driven member includes a protrusion,
   the moving mechanism includes a groove into which the protrusion is fitted, the groove structured to move the driven member in accordance with rotation of the upper link member, and
   the groove has a curved portion.

2. The multi-articulated link knee joint according to claim 1, wherein the position detector and the angle detector are provided at the same link member.

3. The multi-articulated link knee joint according to claim 1, wherein one of the driven member and the moving mechanism is provided at the upper link member, and the other is provided at the lower link member.

4. The multi-articulated link knee joint according to claim 1, further comprising a control device structured to control an auxiliary driver structured to assist motion of the knee unit, wherein the lower link member includes a lower link and a lower leg part connected to the lower link,
the control device is provided at the lower leg part, and the position detector is provided at the lower link.

5. A multi-articulated link knee joint comprising:
a knee unit in which an upper link member is structured to rotate relative to a lower link member by a multi-articulated link mechanism including a plurality of link members including the upper link member and the lower link member;
a driven member structured to move in accordance with rotation of the upper link member;
a position detector structured to detect a position of the driven member, the position detector provided at one of the plurality of link members;
an angle detector structured to obtain a bending angle of the knee unit from the position of the driven member; and
a moving mechanism structured to move the driven member in accordance with rotation of the upper link member,
wherein the driven member includes an abutting member, and
the moving mechanism includes a groove formed such that a depth thereof varies along an extending direction thereof and an energizing member structured to cause the abutting member to abut against a bottom of the groove.

\* \* \* \* \*